US008008385B2

(12) United States Patent
Hill et al.

(10) Patent No.: US 8,008,385 B2
(45) Date of Patent: *Aug. 30, 2011

(54) SOLID ALKYLARYL PHOSPHITE COMPOSITIONS AND METHODS FOR MANUFACTURING SAME

(75) Inventors: Jonathan S. Hill, Manchester (GB); Maurice Power, Manchester (GB); Peter Smith, Avon, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/804,772

(22) Filed: Jul. 28, 2010

(65) Prior Publication Data

US 2011/0028617 A1 Feb. 3, 2011

Related U.S. Application Data

(60) Provisional application No. 61/230,661, filed on Jul. 31, 2009.

(51) Int. Cl.
*C08K 5/526* (2006.01)
(52) U.S. Cl. .......................... 524/150; 524/147; 524/151
(58) Field of Classification Search ........... 524/147–153
See application file for complete search history.

(56) References Cited

U.S. PATENT DOCUMENTS

| 2,733,226 A | 1/1956 | Hunter |
| 3,056,823 A | 10/1962 | Hechenbleikner et al. |
| 5,254,709 A | 10/1993 | Hunter |
| 2009/0326112 A1* | 12/2009 | Gelbin et al. ................. 524/132 |
| 2010/0004363 A1* | 1/2010 | Gelbin et al. ................. 524/150 |
| 2010/0025636 A1* | 2/2010 | Gelbin et al. ............. 252/400.24 |
| 2010/0048782 A1* | 2/2010 | Gelbin et al. ................. 524/147 |
| 2010/0069542 A1* | 3/2010 | Gelbin et al. ................. 524/147 |
| 2010/0076131 A1* | 3/2010 | Gelbin et al. ................. 524/130 |
| 2010/0190900 A1* | 7/2010 | Gelbin et al. ................. 524/132 |
| 2011/0028616 A1* | 2/2011 | Gelbin et al. ................. 524/151 |
| 2011/0028618 A1* | 2/2011 | Gelbin et al. ................. 524/153 |

FOREIGN PATENT DOCUMENTS

| RU | 2 140 938 C1 | 10/1999 |
| RU | 2140938 C1 | 11/2009 |
| WO | WO 2006/066947 A1 | 6/2006 |
| WO | WO 2007/149143 A2 | 12/2007 |

* cited by examiner

*Primary Examiner* — Peter Szekely
(74) *Attorney, Agent, or Firm* — Joseph Suhadolnik

(57) ABSTRACT

The invention is directed to various alkylaryl phosphite compositions that ideally are suitable for use as secondary antioxidants in polymers. In one aspect, the phosphite composition comprises a tris(dialkylaryl)phosphite in an amount from 20 to 93 weight percent; and at least one of: a bis(dialkylaryl) monoalkylaryl phosphite; a bis(monoalkylaryl)dialkylaryl phosphite; and a tris(monoalkylaryl)phosphite. The inventive phosphite composition is a solid at ambient conditions. The invention also relates to alkylate compositions and processes for forming such alkylate compositions and such phosphite compositions.

14 Claims, 1 Drawing Sheet

SOLID ALKYLARYL PHOSPHITE COMPOSITIONS AND METHODS FOR MANUFACTURING SAME

This application claims benefit under 35 USC 119(e) of U.S. Provisional Application No. 61/230,661, filed Jul. 31, 2009, the disclosure of which is incorporated herein by reference.

FIELD OF THE INVENTION

The present invention relates to novel phosphite antioxidants, which are useful, for example, in stabilizing polymers. In particular, the invention relates to novel solid alkylaryl phosphite compositions, to methods of preparing such compositions, and to stabilized polymeric compositions comprising these phosphite compositions.

BACKGROUND OF THE INVENTION

Solid organic phosphite stabilizers are widely used as secondary antioxidants in polymer compositions. One commercially available antioxidant is tris(2,4-di-t-butylphenyl)phosphite, shown below, a solid antioxidant commonly known as Alkanox™ 240, Irgafos™ 168 and Doverphos™ S-480. U.S. Pat. No. 5,254,709, the entirety of which is incorporated herein by reference, describes the synthesis of tris(2,4-di-t-butylphenyl)phosphite by reacting 2,4-di-t-butyl phenol with phosphorus trichloride in the presence of catalyst. The isolated phosphite is described as a white crystalline solid melting between 180-185° C.

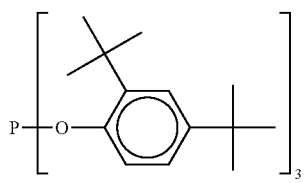

(I)

Tris(2,4-di-t-butylphenyl)phosphite

Tris(2,4-di-t-butylphenyl)phosphite has been demonstrated to effectively reduce peroxide induced oxidative degradation for many polymers including polyolefins, polycarbonates, ABS and polyesters. The trialkylaryl phosphite has low volatility that allows for its use at high temperatures commonly required for processing thermoplastic polymers. Owing to its solid form and concomitant processing limitations, however, tris(2,4-di-t-butylphenyl)phosphite is not well-suited for the stabilization of all polymers and has been demonstrated to plateout during processing of some plastics, in particular low melting point plastics, and forming deposits on processing machinery surfaces.

U.S. Pat. No. 5,254,709 also describes a solid tri(2,4-di-t-amylphenyl)phosphite and a solid mixture derived from 2,4-di-t-amyl phenol and 2,4-di-t-butyl-phenol.

Russian Patent No. RU 2 140 938 discloses a composition of synergists comprising three (2,4-di-t-butylphenyl)phosphites and combinations of other phosphites. The combination includes tri(2-t-butylphenyl)phosphite, tri(4-t-butylphenyl)phosphite, di(4-t-butylphenyl)(2,6-di-t-butylphenyl) phosphite and di(3-t-butylphenyl)(2,4,6-tri-t-butylphenyl) phosphite.

The need exists for novel solid phosphite compositions that are effective secondary antioxidants in polymers and in particular for effective solid phosphite compositions that have good processing characteristics.

SUMMARY OF THE INVENTION

The present invention provides easily processed phosphite compositions that are solid at ambient conditions, have lower melting ranges than tris(2,4-di-t-butylphenyl)phosphite, and are highly useful as secondary antioxidants for stabilizing polymer compositions.

The phosphite compositions typically comprise: (a) a tris (dialkylaryl)phosphite (e.g., tris(2,4-di-t-butylphenyl)phosphite or tris(2,4-di-t-amylphenyl)phosphite) in an amount from 20 to 93 weight percent, e.g., from 25 weight percent to 80 weight percent; and at least one of: (b) a bis(dialkylaryl) monoalkylaryl phosphite; (c) a bis(monoalkylaryl)dialkylaryl phosphite; and (d) a tris(monoalkylaryl)phosphite, wherein the composition comprises components (b), (c) and (d) in combination in an amount from 7 to 80 weight percent, e.g., from 20 weight percent to 75 weight percent, based on the total weight of all phosphites in the composition, and wherein the composition is a solid at ambient conditions. Generally, the composition comprises components (a) and (b) in combination in an amount greater than 51 weight percent, e.g., greater than 74 weight percent, based on the total weight of all phosphites in the composition. In certain embodiments, the alkyl groups in the phosphite compositions are selected from butyl and amyl, for example, t-butyl and t-amyl.

In some embodiments the phosphite composition comprises the bis(dialkylaryl)monoalkylaryl phosphite in an amount from 10 weight percent to 50 weight percent or 15 to 50 weight percent, e.g., from 20 weight percent to 45 weight percent, the bis(monoalkylaryl)dialkylaryl phosphite in an amount from 3 weight percent to 25 weight percent, e.g., from 6 weight percent to 24 weight percent, and the tris(monoalkylaryl)phosphite in an amount of 6% weight percent or less, for example from 0.1 weight percent to 6 weight percent, and often less than 4 weight percent, e.g., less than 2 weight percent.

Generally, the phosphite composition is rich in disubstituted aryl moieties. For example, some aryl moieties are disubstituted and some aryl moieties are monosubstituted and the weight ratio of disubstituted aryl moieties to monosubstituted aryl moieties is from 1.2:1 to 49:1, e.g., from 1.2:1 to 9:1, from 1.5:1 to 8:1 or from 1.8:1 to 7:1. For example, at least 55 weight percent, e.g., at least 60 or at least 65 weight percent, of aryl moieties may be disubstituted with alkyl groups in the ortho-position and the para-position and less than 45 weight percent, e.g., less than 40 or less that 35 weight percent, of aryl moieties may be monosubstituted with an alkyl group in the para-position.

Thus, the solid phosphite composition may be alternately characterized by the weight ratio of dialkylaryl groups to monoalkylaryl groups. In this aspect, the solid phosphite composition comprises two or more phosphite compounds each phosphite compound comprising alkylaryl groups, wherein a first portion of the alkylaryl groups are monoalkylaryl groups and wherein a second portion of the alkylaryl groups are dialkylaryl groups, and wherein the weight ratio of the dialkylaryl groups to monoalkylaryl groups is from 1.2:1 to 49:1, e.g., from 1.2:1 to 9:1, from 1.5:1 to 8:1 or from 1.8:1 to 7:1. The first portion and the second portion may be on the same and/or different phosphite. Typically, the first portion of the alkylaryl groups and the second portion of the alkylaryl groups comprise at least 95 wt. % of the total alkylaryl groups. In this embodiment, as above, the two or more phosphite compounds include: (a) a tris(dialkylaryl)phosphite e.g., tris(2,4-di-t-butylphenyl)phosphite or tris(2,4-di-t-amylphenyl)phosphite), and (b) a bis(dialkylaryl)monoalkylaryl phosphite, and the composition comprises components (a) and (b) in combination in an amount greater than 51 weight percent, e.g., in an amount greater than 74 weight percent, based on the total weight of all phosphites in the composition. The tris(dialkylaryl)phosphite is generally present in an amount ranging from 20 weight percent to 80 weight percent. The phosphite composition may further comprise either or both (c) a bis(monoalkylaryl)dialkylaryl phosphite; and/or (d) a tris(monoalkylaryl)phosphite. Generally the dialkyl groups and the monoalkyl groups are at least one of butyl and amyl.

For each of the above embodiments, the phosphite compositions are solid at ambient conditions but have lower melting ranges than tris(2,4-di-t-butylphenyl)phosphite to facilitate processing and improve solubility in the polymer to be stabilized. Preferably, the composition melts in a range with a lower limit greater than 30° C., greater than 50° C. or greater than 60° C.

The phosphite composition also have low level of 'free phenolics', i.e, unreacted phenolics from the synthesis of the phosphites, for example, often less than 0.5 weight percent free phenolics, or less than 0.1 weight percent free phenolics, based on the total weight of the composition.

The invention also provides stabilized polymeric compositions comprising a polymer and any of the above solid phosphite compositions and processes for stabilizing polymeric compositions by adding composition an effective amount of the above solid phosphite compositions to the polymers. In one embodiment, the polymeric composition is suitable for use in food related applications.

In another embodiment, the invention is to processes for forming the solid phosphite compositions comprising reacting a phosphorus halide with an alkylated phenol composition containing a mixture of alkylated phenols necessary to produce the desired combination of phosphites, wherein the molar ratio of the alkylated phenol composition to the phosphorus halide is preferably from 3.1:1 to 3.7:1.

The alkylated phenol composition comprises a monoalkylphenol and a dialkylphenol, for example, the dialkylphenol is present in an amount ranging from 55 to 98 weight percent, e.g., from 60 to 95 weight percent, or from 70 to 90 weight percent, and the monoalkylphenol in an amount ranging from 2 to 45 weight percent, e.g., from 5 to 40 weight percent, or from 10 to 30 weight percent, based on the total weight of all alkylated phenols in the alkylated phenol composition. The invention is also to these alkylated hydroxyaryl compositions, referred to herein as alkylate compositions, used as intermediates for forming the phosphite compositions. The alkyl moieties in the monoalkylphenol and the dialkylphenol are generally selected from butyl and amyl, for example t-butyl and t-amyl. For example, optionally at least 50 percent or at least 80 weight percent of alkyl moieties in the alkylate composition are t-butyl or tert-amyl. In one embodiment, the monoalkylphenol is a 4-tert-alkylphenol and the dialkylphenol is a 2,4-di-tert-alkylphenol.

The processes optionally further comprise removing unreacted alkylated phenol (free phenolics) from a crude phosphite composition to form the solid phosphite composition.

In another embodiment, the invention is to alkylated hydroxyaryl compositions, referred to herein as alkylate compositions, suitable as intermediates for forming the above described phosphite compositions. In one aspect, the alkylate composition comprises a dialkylphenol in an amount ranging from 60 to 90 weight percent, e.g., from 65 to 75 weight percent; and a monoalkylphenol in an amount ranging from 10 to 40 weight percent, e.g., from 25 to 35 weight percent, the weight percentages being based on total weight of all alkylated phenols in the alkylate composition. The alkyl moieties in the monoalkylphenol and the dialkylphenol are preferably selected from various butyl and amyl isomers, for example sec-butyl, t-butyl, sec-amyl, t-amyl etc. For example, optionally at least 50 percent or at least 80 weight percent of alkyl moieties in the alkylate composition are t-butyl or tert-amyl. In a one embodiment, the monoalkylphenol is a 4-tert-alkylphenol and the dialkylphenol is a 2,4-di-tert-alkylphenol. In many embodiments, the presence of other isomers, e.g., sec-alkyl, iso-alkyl etc are beneficial and smaller amounts of these materials are often present in both the alkylate and resuling phosphite compositions.

The invention is also directed to processes for forming such alkylate compositions. For example, by contacting one or more olefins with a phenol in the presence of a catalyst and under conditions effective to form the alkylate composition desired. In many embodiments, the alkylate composition comprises, in addition to the dialkylphenol, monoalkylphenol etc, from 0-3% unsubstituted phenol, e.g., 0.01 to 3% phenol, which may be removed, for example by distillation, or carried forward into the phosphite forming reaction with the phosphorous halide.

BRIEF DESCRIPTION OF THE DRAWING

The present invention will be better understood in view of appended non-limiting FIG. 1, which presents an approximated plot of viscosity of alkylaryl phosphite compositions as a function of dialkylaryl moiety content and monoalkylaryl moiety content.

DETAILED DESCRIPTION OF THE INVENTION

Figure 1:
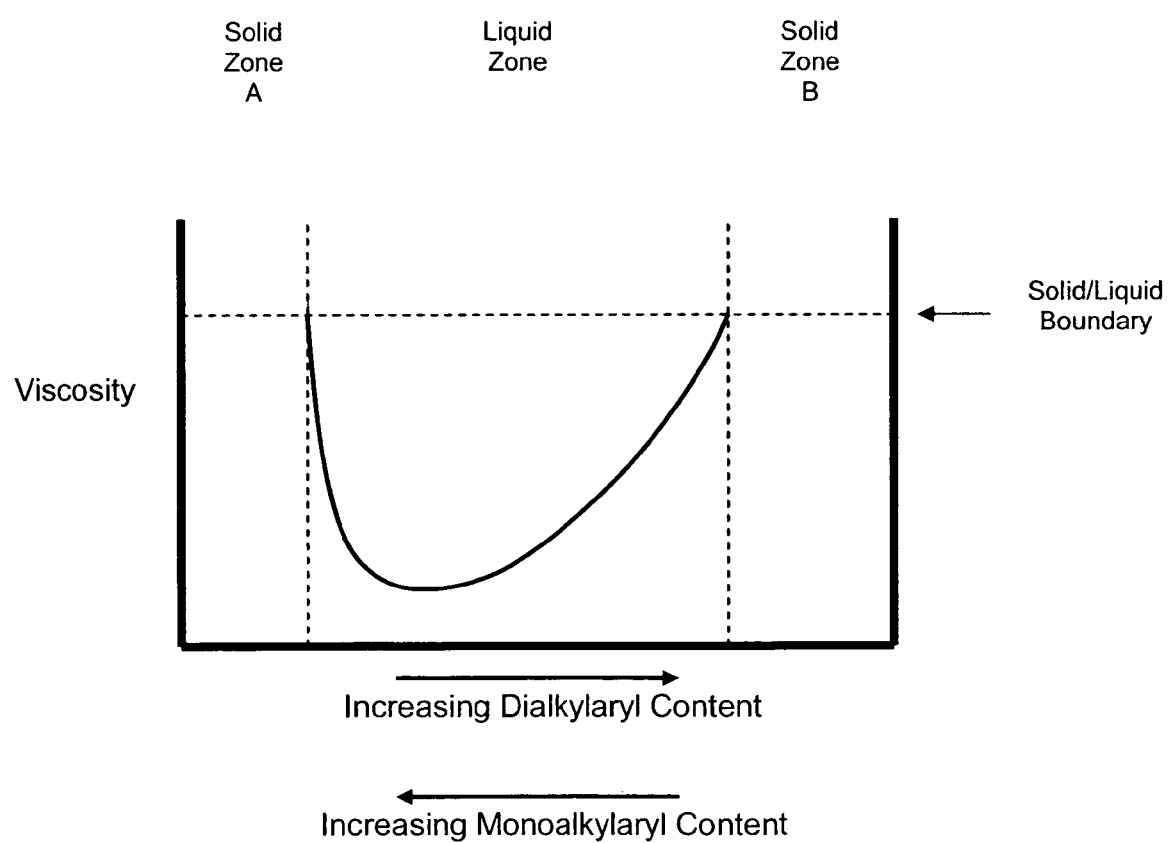

The invention is directed to phosphite compositions that are solid at ambient conditions. The phosphite compositions comprise two or more phosphite compounds comprising alkylated aryl moieties, a majority of which are dialkylated. Typically, the weight ratio of the dialkylaryl groups to monoalkylaryl groups ranges from 1.2:1 to 9:1, e.g., from 1.5:1 to 8:1 or from 1.8:1 to 7:1. The invention is also directed to processes for forming the above-described compositions, to alkylated hydroxyaryl intermediates for making such compositions and to processes for forming such alkylated hydroxyaryl intermediates.

Incorporating the inventive alkylaryl phosphite compositions into polymeric compositions improves the characteristics and/or properties of the resultant polymeric compositions. As an example, melt flow index, and/or cross-linking induction time of the polymeric composition may be significantly increased as well as color as measured by yellowness index (YI). The presence of multiple phosphite compounds in the phosphite compositions of the invention results in different steric environments around the central phosphorus atom and allows for a range of hydroperoxide scavenging, which ideally provides more effective stabilization.

In addition to their stabilizing properties, the phosphite compositions of the invention have highly desirable processing characteristics and are easily incorporated into a variety of polymers. For example, the solid phosphite compositions have relatively low melting point ranges and may be liquefied at low temperatures. Owing to their compositional diversity, the solid phosphite compositions also have high solubility in various polymers reducing, in particular, plateout when compared with pure tris(2,4-di-alkylaryl)phosphites such as tris (2,4-di-t-butylphenyl)phosphite. The solid phosphite compositions of the invention are also more readily processed into different forms and blends than many pure alkylaryl phosphite compounds.

Alkylaryl Phosphite Compositions

The alkylaryl phosphite compositions of the invention are solid at ambient conditions. By ambient conditions, it is meant 25° C. and 1 atmosphere pressure.

In one embodiment, the invention is to a phosphite composition, comprising: (a) a tris(dialkylaryl)phosphite in an amount from 20 to 93 weight percent, e.g., from 30 to 70 weight percent; and at least one of: (b) a bis(dialkylaryl) monoalkylaryl phosphite; (c) a bis(monoalkylaryl)dialkylaryl phosphite; and (d) a tris(monoalkylaryl)phosphite. The composition comprises components (b), (c) and (d) in combination in an amount from 7 to 80 weight percent, e.g., from 30 to 70 weight percent, based on the total weight of all phosphites in the composition. In addition, the composition preferably comprises components (a) and (b) in combination in an amount greater than 51 weight percent, e.g., greater than 74 weight percent, based on the total weight of all phosphites in the composition.

As indicated above, the aryl moieties in a majority, of the phosphite compounds in the phosphite composition are substituted with one or more alkyl groups, such as, for example, $C_1$-$C_{18}$, e.g., $C_4$-$C_{10}$, or $C_3$-$C_5$ alkyl groups. In this aspect, the alkyl substituent(s) on the aryl moieties may be selected from straight-chain or branched $C_1$-$C_{18}$ alkyl, e.g., $C_1$-$C_{10}$ alkyl, $C_1$-$C_8$ alkyl, $C_4$-$C_{10}$ alkyl, $C_3$-$C_5$ alkyl, $C_4$-$C_6$ alkyl, $C_5$ alkyl, or $C_4$ alkyl. The one or more alkyl substituent include, for example, methyl, ethyl, propyl, butyl, amyl, hexyl, heptyl, octyl, nonyl (although less preferred), decyl, undecyl, dodecyl, tridecyl, tetradecyl, pentadecyl, hexadecyl, heptadecyl, octadecyl, and isomers thereof. For example, the alkyl substituents are $C_4$ groups, i.e., n-butyl, sec-butyl, iso-butyl, and/or t-butyl and/or $C_5$ groups, i.e. n-amyl, sec-amyl, iso-amyl, neo-amyl, tert-amyl, 1-methylbutyl and/or 1,2-dimethylpropyl). In particular embodiments, the alkyl groups are branched or highly branched, for example, t-butyl and tert-amyl.

In one embodiment, the phosphite composition is comprised primarily of phosphites having aryl moieties that are disubstituted. In this embodiment, the phosphite composition comprises: (a) a tris(dialkylaryl)phosphite in an amount from 20 to 90 weight percent, e.g., from 20 to 80 weight percent or 30 to 70 weight percent; and (b) a bis(dialkylaryl)monoalkylaryl phosphite, wherein the composition comprises components (a) and (b) in combination in an amount greater than 51 weight percent, e.g., greater than 74 weight percent, based on the total weight of all phosphites in the composition and optionally (c) a bis(monoalkylaryl)dialkylaryl phosphite and/ or (d) a tris(monoalkylaryl)phosphite, although in minor amounts.

The relative types and amounts of phosphite compounds contained in the phosphite compositions of the invention may vary somewhat so long as the phosphite composition is a solid at ambient conditions. In terms of ranges, for example, the phosphite composition comprises:

(a) tris(dialkylaryl)phosphite (optionally tris(2,4-di-t-butylphenyl)phosphite or tris(2,4-di-t-amylphenyl)phosphite) in an amount from 17 to 96 weight percent, e.g., from 20 to 90 weight percent, from 25 to 88 weight percent, or from 30 to 70 weight percent;

(b) bis(dialkylaryl)monoalkylaryl phosphites (optionally bis(2,4-di-t-butylphenyl)-4-t-butylphenyl phosphite or bis(2,4-di-t-amylphenyl)-4-t-amylphenyl phosphite) in an amount of from 4 to 73 weight percent, e.g., from 40 to 60 weight percent, from 24 to 50 weight percent or from 32 to 42 weight percent;

(c) optionally bis(monoalkylaryl)dialkylaryl phosphites (optionally bis(4-t-butylphenyl)-2,4-di-t-butylphenyl phosphite or bis(4-t-amylphenyl)-2,4-di-t-amylphenyl phosphite), preferably in an amount less than 33 weight percent, e.g., from 3 to 25 weight percent or from 6 to 24 weight percent; and (d) optionally tris(monoalkylaryl)phosphites (optionally tris(4-t-butylphenyl)phosphite or tris(4-t-amylphenyl) phosphite), preferably in an amount less than 9 weight percent, for example 6% weight percent or less such as from 0.1 weight percent to 6 weight percent, and often less than 4 weight percent or less than 2 weight percent.

Unless otherwise indicated, the weight percent of these components is determined based on the total weight of all alkylaryl phosphite compounds in the solid phosphite composition.

As indicated above, the solid phosphite compositions of the invention may also be characterized in terms of the percent aryl moieties that are disubstituted (e.g., 2,4-disubstituted). For example, preferably at least 55 weight percent, e.g., at least 60 weight percent, or at least 65 weight percent, of the aryl moieties are disubstituted, preferably in the ortho and para position when the aryl moiety is phenyl. In terms of ranges, preferably from 55 to 98 weight percent, e.g., from 60 to 80 weight percent or from 65 to 75 weight percent, of the aryl moieties are disubstituted (e.g., 2,4-disubstituted when the aryl moiety is a phenolic). Conversely, preferably less than 45 weight percent of the aryl moieties are monosubstituted (e.g., monosubstituted in the 2-(ortho) and/or 4-(para) positions when the aryl moiety is a phenolic), optionally less than 40 weight percent, or less than 35 weight percent. In terms of ranges, optionally from 2 to 45 weight percent of the aryl moieties are monosubstituted (e.g., monosubstituted in the 2- and/or 4-positions when the aryl moiety is a phenolic), e.g., from 5 to 40 weight percent or from 10 to 35 weight percent. In terms of ratios, some aryl moieties are disubstituted and some aryl moieties are monosubstituted and the weight ratio of disubstituted aryl moieties to monosubstituted aryl moieties preferably is from 1.2:1 to 49:1, e.g., from 1.2:1 to 9:1, from 1.5:1 to 8:1 or from 1.8:1 to 7:1.

It has now been discovered that at the high dialkylaryl moiety contents described herein, highly processable solid phosphite compositions may be formed. FIG. 1 presents an approximated plot of viscosity of alkylaryl phosphite compositions as a function of dialkylaryl aryl moiety content and monoalkyl aryl moiety content (e.g., the ratio of dialkylaryl moieties to monoakylaryl moieties). As shown, viscosity and the physical state of various alkylaryl phosphite compositions are highly dependent on dialkylaryl moiety content and monoalkylaryl moiety content. At the left side of FIG. 1, it can be seen that at very low dialkylaryl moiety content and at high monoalkylaryl moiety content, the phosphite composition is a solid at ambient conditions, as shown by "Solid Zone A." As dialkylaryl moiety content increases relative to monoalkylaryl moiety content, the phosphite composition becomes liquid in form as shown by the "Liquid Zone." It should be noted that only a narrow region of the Liquid Zone is a mobile stable liquid composition capable of withstanding repeated freeze/thaw cycles as the regions on the right side of the Liquid Zone tend to form highly viscous meta-stable liquids. As dialkylaryl moiety content continues to increase relative to monoalkylaryl moiety content, solid phosphite compositions may be formed, as shown by "Solid Zone B." Solid Zone B is the region representing the phosphite compositions of the present invention.

The major species in such phosphite compositions typically will be the tris(dialkylaryl)phosphite and the bis(dialkylaryl)monoalkylaryl phosphite compounds rather than the bis(monoalkylaryl)dialkylaryl phosphite and tris(monoalkylaryl)phosphite compounds since the latter compounds are comprised primarily of aryl moieties that are monoalkylated. Thus, the phosphite composition typically comprises the tris (dialkylaryl)phosphite, e.g., tris(di-t-butylphenyl)phosphite or tris(di-t-amylphenyl)phosphite, and the bis(dialkylaryl) monoalkylaryl phosphite, e.g., bis(di-t-butylphenyl)mono-t-butylphenyl phosphite or bis(di-t-amylphenyl)mono-t-amylphenyl phosphite, in an amount greater than 51 weight percent, e.g., greater than 74 weight percent, based on the total weight of all phosphites in the composition. In one aspect, the major ingredient in the phosphite composition is a tris(dialkylaryl)phosphite (e.g., tris(2,4-di-t-butylphenyl) phosphite or tris(2,4-di-t-amylphenyl)phosphite). In another aspect, the major ingredient in the phosphite composition is a bis(dialkylaryl)monoalkylaryl phosphite (e.g., bis(2,4-di-t-butylphenyl)-4-t-butylphenyl phosphite or bis(2,4-di-t-amylphenyl)-4-t-amylphenyl phosphite).

In preferred aspects, the aryl moiety is phenyl and at least 55 weight percent, e.g., at least 60 weight percent, or at least 65 weight percent, of the aryl moieties are disubstituted in the 2- and 4-positions, preferably with a butyl group, e.g., t-butyl, or an amyl group, e.g., t-amyl. In addition, preferably at least 10 weight percent, at least 20 weight percent, or at least 25 weight percent of the aryl moieties are monosubstituted in the 4-position, often with a butyl group, e.g., t-butyl, or an amyl group, e.g., t-amyl, although there may be other alkyl groups and other isomers present, such as sec-butyl, n-butyl, iso-butyl, n-amyl, sec-amyl neo-amyl etc.

In addition, the presence of multiple phosphite compounds in the phosphite composition can lead to an improvement in compatibility/solubility when compared to pure tris(2,4-di-t-alkylphenyl)phosphites, e.g., tris(2,4-di-t-butylphenyl)phosphite or tris(2,4-di-t-amylphenyl)phosphite. The improved solubility of the phosphite compositions provides lower migration of the phosphite composition to the surface of the resulting polymer product thereby yielding more stable polymer products. The improved solubility also: (i) reduces plateout (or build up of solid material in the polymer processing plant), (ii) improves gloss on polymer film surfaces, (iii) improves ink adhesion for printing on polymer films and articles, and (iv) improves sealability of plastic films and articles.

The phosphite composition of the present invention may be characterized by its melting point. As indicated above, the phosphite compositions of the invention are solid at ambient conditions. By "solid," it is meant that the phosphite composition has a melting point greater than 25° C., for example greater than 30° C., greater than 40° C., greater than 50° C., greater than 60° C. or greater than 70° C. Actually, as the compositions are mixtures, 'melting points' in this regard are melting ranges beginning at a defined lower limit, e.g. greater than 30° C. The phosphite composition is melted during processing so that it may be incorporated into the polymer to be stabilized.

The phosphite composition generally has melts in a temperature range lower than the temperature at which tris(2,4-di-t-butylphenyl)phosphite melts, i.e., about 180-185° C. For example, the phosphite composition of the present invention will become molten at temperatures less than 180° C., e.g., less than 175° C., less than 170° C., or less than 165° C. For example, ranges, the phosphite composition will have a melting point range from 40° C. to 180° C., e.g., from 60° C. to 175° C., from 60° C. to 120° C., or higher ranges such as from 100° C. to 180° C. or from 140° C. to 180° C. Lower melting points are often preferred so that the phosphite compositions may be easily liquefied during processing and more homogenously dispersed in the polymer to be stabilized. Thus, the phosphite composition is often highly soluble in the polymer to be stabilized, ideally more soluble in the polymer to be stabilized than pure tris(2,4-di-t-butylphenyl)phosphite, consequently reducing problems associated with plate out and blooming.

In one embodiment, the phosphite composition comprises compounds having the structure:

(II)

wherein $R_1$, $R_2$ and $R_3$ are independently selected alkylated aryl groups. In one embodiment, the aryl moiety present in the phosphites of the present invention, e.g., $R_1$, $R_2$, or $R_3$, is an aromatic moiety of from 6 to 18 carbon atoms, e.g., phenyl, naphthyl, phenanthryl, anthracyl, biphenyl, terphenyl, o-cresyl, m-cresyl, p-cresyl, xylenol(s), and the like, typically phenyl.

The aromatic moieties may be mono, di or tri substituted in one or more of the ortho-, meta- and/or para-positions, typically one or more of the ortho- and/or para-positions, with an alkyl group, provided that a number majority or a weight majority of the aromatic moieties are disubstituted, preferably disubstituted in the 2- and 4-positions where the aromatic moiety is a phenolic. As indicated above, the phosphite composition should comprise either or both tris(dialkylaryl) phosphite and/or a bis(dialkylaryl)monoalkylaryl phosphite. Generally, the phosphite composition further comprises either or both a bis(monoalkylaryl)dialkylaryl phosphite and/or a tris(monoalkylaryl)phosphite, although such compounds ideally are present in minor amounts (less than 50 wt. %) if at all.

In some embodiments, the phosphite composition comprises phosphite compounds that are alkylated with $C_4$ and/or $C_5$ substituents and in some particular embodiments do not contain phosphites that contain aryl moieties that are substituted with other substituents. In some embodiments, the phosphite composition comprises phosphite compounds other than components a, b, c and d, but in low amounts, for example, the phosphite composition may comprise from 0.1 to 5% weight percent other phosphites selected from the group consisting of phosphites containing trialkylaryl moieties and phosphites containing unsubstituted aryl moieties, for example, 0.1 to 4 weight percent of all aryl moieties comprised by the phosphites may be trialkyl aryl moieties.

In a preferred embodiment, the phosphite composition is substantially free of $C_8$-$C_{10}$ alkyl substituents. Often the phosphite composition is substantially free of nonylaryl phosphite compounds, meaning the phosphite composition comprises (if any) less than 100 wppm, e.g., less than 50 wppm or less than 20 wppm, nonylaryl phosphite compounds, defined herein as a phosphite compound having at least one nonylaryl moiety. The term "wppm" refers to parts per million based on the total weight of the phosphite composition.

In one embodiment, substantially all of the phosphite compounds in the phosphite composition, e.g., at least 90 wt. %, at least 95 wt. %, or at least 99 wt. % of the phosphite compounds in the phosphite composition, are alkylaryl phosphite compounds. As such, the aryl moieties of the phosphite(s) are alkyl substituted aryl groups, e.g., $C_4$-$C_5$-alkylaryl groups. In a preferred embodiment, at least 95 weight percent, at least 98 weight percent or at least 99 weight percent of the aryl moieties are substituted with one or more t-butyl or tert-amyl groups. Similarly, in a preferred embodiment, at least 95 weight percent, e.g., at least 98 weight percent or at least 99 weight percent of the alkyl substituents are t-butyl or tert-amyl substituents. In another embodiment, few (if any) of the phosphite compounds are alkyl substituted, e.g., less than 10%, less than 5%, less than 2% or less than 1% are alkyl substituted. Alkyl phosphites refers to phosphites having alkyl groups, e.g., propyl groups, bonded directly to the oxygen atom, such as trialkyl phosphite.

Referring to the phosphites of structure (II), in one embodiment, the alkylaryl moieties, e.g., $R_1$, $R_2$, and $R_3$, are independently selected alkylated phenyl groups of the structure (III):

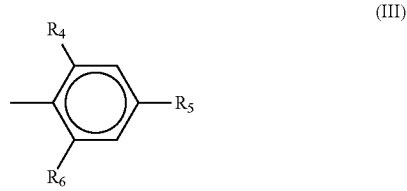

(III)

wherein $R_4$, $R_5$, and $R_6$ are independently selected from the group consisting of hydrogen and $C_1$-$C_8$ alkyl, e.g., methyl, ethyl, propyl, butyl, amyl, hexyl, heptyl, octyl, and isomers thereof, for example, at least group is butyl or amyl, for example, t-butyl or t-amyl. A number majority or a weight majority of the aryl groups in the phosphite composition are disubstituted, preferably containing alkyl groups in both the ortho and para positions, e.g., wherein $R_5$ and $R_6$, are alkyl groups and $R_4$ is hydrogen. In a preferred embodiment, $R_4$ and $R_6$ are hydrogen, and $R_5$ is an alkyl group for at least some (but preferably a minority) of the aryl groups in the phosphite composition. In some embodiments, the alkyl groups have no α-hydrogen atoms, e.g., the alkyl groups are tert-alkyl groups.

In another embodiment, $R_1$, $R_2$, and $R_3$ of structure (II) are independently selected alkylated aryl groups of the structure:

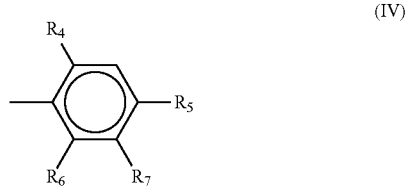

(IV)

wherein $R_4$, $R_5$, and $R_6$ are defined above and $R_7$ is hydrogen or methyl, provided that one of $R_4$, $R_5$, $R_6$, and $R_7$ is methyl and that at least two of $R_4$, $R_5$, $R_6$, and $R_7$ are not hydrogen. As indicated above, preferably a majority, preferably a weight majority, of the alkylaryl groups are disubstituted. For example, the phosphites may be formed, for example, by the reaction of one or more alkylated (e.g., amylated or butylated) cresol compounds with $PCl_3$. In this embodiment, the terms dialkyl and disubstituted refer to alkyl groups other than the cresyl methyl group.

As indicated above, the phosphite compositions of the invention include phosphite compounds having aryl moieties that are dialkylated and monoalkylated, whether on the same or different molecules. In some embodiments, few if any of the aryl moieties are tri-substituted. For example, in some embodiments fewer than 3 wt. % of the aryl moieties are trisubstituted, e.g., fewer than 2 wt. %, or fewer than 1 wt. %. In another embodiment, the phosphite compositions are completely free of trisubstituted aryl moieties, meaning no trisubstituted aryl moieties are detectable.

Similarly, few if any of the aryl moieties are monosubstituted in the ortho position. Preferably, the aryl moieties are monosubstituted in the ortho position in an amount less than 3 wt. %, e.g., less than 2 wt. % or less than 1 wt. %.

Preferably, the phosphite composition has a low level or is substantially free, i.e., 0 to 5% by weight based on the total phosphite composition, of phenolics (e.g., phenol, cresols or xylenols), whether alkylated or unalkylated, referred to herein as "free phenolics" or "free phenols", when contained in the phosphite composition. These free phenols of the invention are generally unreacted phenolics from the reaction with phosphorous trihalide to form the phosphite compounds and reflect the structures of the alkylated aryl groups of the phosphites. In terms of amounts, the phosphite composition preferably comprises less than 5 wt. %, e.g., less than 3 wt. % or less than 1 wt. %, of free phenolics, based on the total weight of the phosphite composition. Unwanted free phenolics may be removed, for example, by distillation.

Extremely low levels of free phenolics may be achieved, for example, by employing a wiped-film molecular (Short-Path) still, wiped film evaporator (WFE), thin film evaporator, or similar equipment. Thus, the phosphite composition may comprise less than 0.5 wt. %, e.g., less than 0.2 wt. % or less than 0.1 wt. %, of free phenolics, based on the total weight of the phosphite composition. Such low free phenolic levels may be particularly desirable for use in high temperature processing, for example, as typically required for polypropylene processing, in order to reduce volatile organic loss or fuming. See, e.g., U.S. Pat. No. 5,531,401, the entirety of which is incorporated herein by reference.

Phosphites are often used in combination with certain hindered phenol primary antioxidants, and the present phosphite compositions may also be used in combination with such primary antioxidants.

In addition, the phosphite composition is preferably substantially free of phosphite compounds having unsubstituted aryl moieties, e.g., triphenylphosphites, bis(phenyl)alkylphenyl phosphites or bis(alkylphenyl)phenyl phosphites. In terms of amounts, the phosphite composition preferably comprises less than 3 wt. %, e.g., less than 2 wt. % or less than 1 wt. %, phosphite compounds having at least one unsubstituted aryl moiety, based on the total weight of the phosphite composition.

In other embodiments, the phosphite composition is substantially free of phosphite compounds having aryl groups that are substituted with alkyl groups having hydrogen atoms in the α position. That is, in preferred embodiments, at least 95%, at least 98% or at least 99% of the aryl moieties are substituted with alkyl groups having tertiary α-carbons, most preferably t-butyl and tert-amyl.

In some embodiments, the phosphite composition has a phosphorous content that is at least 4.0 mole %, e.g., at least 4.2 mole %, at least 4.5 mole %, at least 4.8 mole % or at least 5.0 mole %. For example, the overall phosphorus content of the phosphite composition typically will range from 4.0 to 5.5 mole %, e.g., from 4.2 to 5.4 or from 4.5 to 5.2 of all phosphorous-containing compounds in the phosphite composition. For butylaryl phosphite compounds, the phosphite composition preferably has an overall phosphite content ranging from 4.8 to 5.4 mole %, and for amylaryl phosphite compounds, the phosphite composition preferably has an overall phosphite content ranging from 4.2 to 4.9 mole %.

In some preferred embodiments, the phosphite composition includes one or more hydrolytic stabilizers. Preferred stabilizers include amines of the structure:

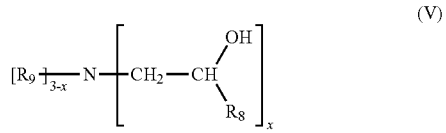

(V)

wherein x is 1, 2 or 3, preferably 1 or 2; $R_8$ is selected from the group consisting of hydrogen, and straight or branched $C_1$-$C_6$ alkyl, and $R_9$ is selected from the group consisting of straight or branched $C_1$-$C_{30}$ alkyl. Preferably $R_8$ is selected from the group consisting of straight or branched $C_1$-$C_4$ alkyl, e.g., methyl or ethyl. Preferably $R_9$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_9$ is straight or branched $C_5$-$C_{20}$ alkyl, e.g., $C_{12}$-$C_{18}$ alkyl. In one embodiment, x is 2 and $R_9$ is straight or branched $C_{10}$-$C_{20}$ alkyl, e.g., $C_{12}$-$C_{18}$ alkyl.

In one aspect the amine is selected from the group consisting of the triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol) amine, octyl-bis(2-propanol)amine, nonyl-bis(2-propanol) amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available amines include Armostat™ 300 and Armostat 1800.

The amine may be present in an amount of from 0.01 to 5 wt. %, e.g., from 0.1 to 1.5 wt. % or from 0.2 to 0.8 wt. %, based on the total weight of the phosphite composition.

Additional hydrolytic stabilizers include epoxies such as epoxidized soybean oil (ESBO) commercially available as Drapex™ 39, Drapex 392, Drapex 4.4, and Drapex 6.8 or polycarbodiimides, commercially available as Stabaxol™ P.

Processes for Making Phosphite Compositions

The present invention also relates to processes for making the above-described solid phosphite compositions and to novel alkylate compositions comprising at least two different alkylated hydroxyaryl compounds used in such processes. For example, the solid phosphite compositions may be made in the direct reaction of a phosphorus trihalide, e.g., phosphorus trichloride, and two or more alkylated hydroxyaryl compounds, e.g., an "alkylate composition." The hydroxyaryl compound may be any aromatic compound having at least one hydroxyl group, including, for example, phenol, cresols, xylenols, and mixtures thereof.

Generally, the alkylate composition comprises a dialkyl phenol, e.g., a 2,4-dialkyl phenol such as 2,4-di-t-butylphenol or 2,4-di-t-amylphenol, and a monoalkyl phenol, e.g., a 4-alkyl phenol such as 4-t-butylphenol or 4-t-amylphenol. The dialkylphenol, e.g., 2,4-di-tert-alkylphenol, is typically present in an amount ranging from 55 to 98 wt. %, e.g., from 55 to 95 wt. %, from 60 to 95 wt. %, or from 70 to 90 wt. %, based on the total weight of the alkylate composition. The dialkylphenol, e.g., 2,4-di-tert-alkylphenol, may be present in amounts greater than 55 wt. %, e.g., greater than 60 wt. %, greater than 65 wt. % or greater than 70 wt %. The monoalkyl phenol, e.g., 4-alkylphenol, is preferably present in an amount ranging from 2 to 45 wt. %, e.g., from 5 to 40 wt. %, from 10 to 30 wt. %, based on the total weight of the alkylate composition. The alkylate composition preferably has a weight ratio of dialkylphenols to monoalkylphenols of from 1.2:1 to 49:1, e.g., from 1.5:1 to 9:1 or from 1.8:1 to 8:1. The alkylate composition may optionally contain minor amounts of other alkyl phenols, such as but not limited to a 2-alkyl phenol and/or a non-alkylated phenol.

The alkylate composition is conveniently formed by contacting one or more hydroxyaryl compounds, e.g., phenols or cresols, with one or more olefins, e.g., butenes and/or amylenes, such as isobutylene or isoamylene, in the presence of a catalyst and under conditions effective to form the alkylate composition. The one or more olefins preferably contain from 2 to 18 carbons, e.g., from 2 to 8 carbons, or from 4 to 6 carbons. As an alternative to using an olefin alkylating agent, one or more alkyl halides, alcohols, MTBE or TAME may be employed. The alkylating agent that is employed may comprise or be derived from a hydrocarbon stream comprising alkanes and alkenes, such as a petrochemical raffinate stream from a $C_4$ or $C_5$ fraction, or a dehydrogenation reaction product of an alkane, e.g., isobutane or isopentane. In this aspect, the alkanes pass through the alkylating process unaltered and may be easily separated from the product alkylate composition.

The ratio of hydroxyaryl compounds to olefin is such that the resulting alkylate composition is suitable for conversion to the desired phosphite composition. In some exemplary embodiments, the molar ratio of the one or more olefins, e.g., isobutylene or isoamylene, to the hydroxyaryl compound, e.g., phenol or cresol, ranges from 1.5:1 to 6:1, e.g., from 1.5:1 to 5:1 or from 1.75:1 to 3:1, although these ratios may vary somewhat depending, for example, on the choice of olefin, the catalyst employed in the alkylation process and the desired composition and viscosity for the ultimately formed phosphite composition to be formed from the alkylate composition.

Conditions for the alkylation process may vary widely, in some preferred embodiments the reaction of the phenol and the olefin occurs in an inert atmosphere (e.g., under nitrogen) at a temperature of from 60 to 160° C., e.g., from 70 to 145° C. or from 80 to 140° C., at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour.

The alkylation usually is performed in the presence of a catalyst, suitable for forming an alkylate composition that is rich in dialkylated hydroxyaryl compounds, e.g., 2,4-dialkylphenols such as 2,4-di-t-butylphenol or 2,4-di-t-amylphenol. The catalyst may, for example, be selected from the group consisting of acid clay catalyst, cationic ion exchange resins, Brönsted acids, e.g., sulfuric acid, trifluoromethanesulfonic acid (triflic acid) and phosphotungstic acid, or Lewis acids, e.g., $BF_3$. Suitable commercial acid clay catalysts include Fulcat™ 22B. Sulfonic acid-type cation-exchange resin catalysts useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin, including commercially available cation exchange resins, for example styrene-divinylbenzene type strong acid ion exchange resins such as Dowex™ 50WX4, Dowex 50WX2, Dowex M-31, Dowex Monosphere M-31, Dowex DR-2030 and Dowex Monosphere DR-2030 catalysts. Other appropriate commercial resins include: Amberlyst™ 15, Amberlyst 131, Amberlyst 35, Amberlyst 36, and A21; Diaion™ WA30, Diaion SK104, Diaion SK1B, Diaion PK208, Diaion PK212 and Diaion PK216; Tulsion™ T-38, Tulsion T-62, Tulsion T-66, Tulsion T-3825 and Tulsion T-3830; Lewatit™ K1131, Lewatit K1221, Lewatit K1261 and Lewatit SC 104; Indion™ 180 and Indion 225; and Purolite™ CT-175, Purolite™ CT-169, and Purolite™ CT-275.

In one embodiment, a batch alkylate synthesis takes place in a pot-type reactor. In another embodiment, the alkylate synthesis is conducted on a continuous basis in a continuous type reactor. In alternative embodiments, the reaction is conducted in a fixed bed reactor.

In one aspect of the process, any free phenolic compounds that are not reacted with the olefin may be removed from the mixture of reaction products through distillation at a temperature, for example, of from 70 to 160° C. and at a pressure of from 1 to 10 mbar.

In some embodiments, a mixed olefin (e.g., $C_4$ and $C_5$) and/or mixed phenolic feedstock may be used to form a diverse alkylate composition, which may be desired to ultimately form a more diverse phosphite composition. Thus, a mixture of lower alkenes (e.g., two or more $C_3$-$C_6$ olefins, such as a mixture of butylenes, a mixture of amylenes, a mixture of butylene and amylene, propylene and amylene or propylene and butylene) may be reacted with the phenolic compound either in parallel (feed in olefin A and B at the same time) or consecutively (i.e. olefin A is reacted first followed by olefin B).

In one embodiment, the alkylate composition formed from the above-described alkylate composition synthesis process is further reacted with a phosphorus trihalide, for example phosphorus trichloride or phosphorus tribromide, with or without catalyst, to form the solid phosphite composition. As the dialkylated hydroxyaryl compounds are more bulky than monoalkylated hydroxyaryl compounds, a catalyst preferably is used that facilitates the reaction between the dialkylated hydroxyaryl compounds with the $PCl_3$. Useful catalysts include, but are not limited to pyridine, N,N-dimethyldodecylamine, dilauryl methyl amine, trialkylamine, and the hydrochloride salts thereof. The molar ratio of alkylate composition (i.e., alkylated phenol compounds) to phosphorus trihalide preferably is from 3:1 to 5:1, e.g., from 3:1 to 4:1 or from 3.1 to 3.7:1.

The reaction of the alkylate composition with the phosphorus trihalide may be conducted under an inert atmosphere (e.g., nitrogen) at a temperature of from 5 to 70° C., e.g., from 40 to 70° C. or from 50 to 70° C. The phosphorus trihalide may be charged to the reactor and the alkylate composition may be added thereto. In this case, preferably, the temperature is held at or below 70° C. during the addition of the phosphorus trihalide to the alkylate composition to prevent refluxing the phosphorus trihalide. After the addition of phosphorus trihalide, the temperature is optionally held for 10 minutes to 12 hours, e.g., from 30 minutes to 10 hours, or from 1 hour to 3 hours. The reaction preferably is conducted at a pressure of 0.8 to 4 atm, e.g., from 0.9 to 3 atm or from 1 to 2 atm. Optionally, the alkylate composition may be charged to the reactor and the phosphorus trihalide added thereto. Next, the temperature may be increased to a ramped temperature ranging from 70° C. to 200° C., e.g., from 80° C. to 150° C. or from 90° C. to 120° C. Preferably, the reaction is held at the ramped temperature for from 10 minutes to 12 hours, e.g., from 30 minutes to 10 hours, or from 1 hour to 3 hours. The reaction preferably is conducted at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total halide content in the reaction mixture is less than 50 wppm, e.g., less than 25 wppm or less than 10 wppm.

In one aspect of the process, any free phenolics that are not reacted with the phosphorus trihalide may be liberated by raising the reaction temperature to up to 275° C., e.g., up to 250° C. or up to 225° C., and in a vacuum at a pressure of 0.0001 to 0.1 atm. In one embodiment, a wiped-film molecular (Short-Path) still, wiped film evaporator (WFE), thin film evaporator, or similar equipment may be used to further remove the free phenolics to the very low levels indicated above.

In one embodiment, the phosphite composition is formed in one or more neutral solvents. Typical solvents that may be employed include toluene, xylene, methylene chloride, heptane, chloroform, and benzene.

In one embodiment, the solid phosphite compositions of the present invention are obtained in a direct chemical reaction, in which the molar ratio of the various alkylated hydroxyaryl compounds is adjusted to yield a phosphite composition that is a solid at ambient conditions. A schematic of one reaction method that may be employed to form such phosphite compositions is as follows.

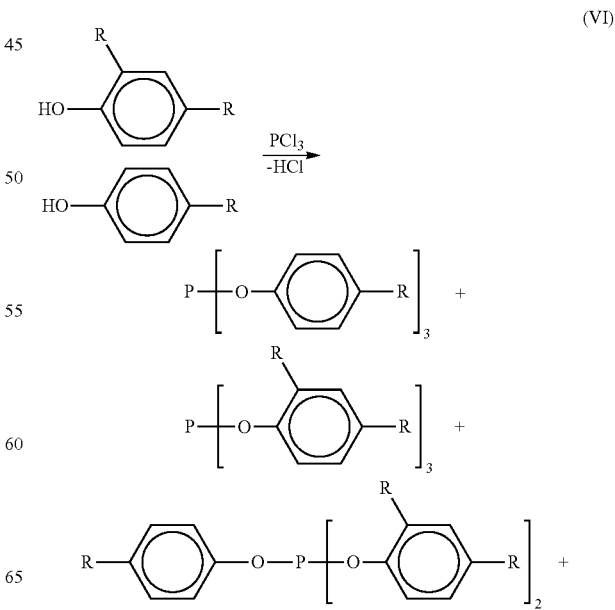

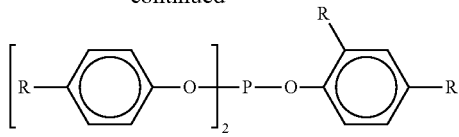

wherein R is independently $R_4$, $R_5$, and $R_6$ as defined above. Preferably, since the alkylate composition is comprised primarily of disubstituted hydroxyaryl compounds, e.g., 2,4-di-t-butylphenol or 2,4-di-t-amylphenol, the major components formed in the resulting phosphite composition are the tris(dialkylaryl)phosphite and the bis(dialkylaryl)monoalkylaryl phosphite, e.g., (2,4-dialkylphenyl)phosphite and the bis(2,4-dialkylphenyl)-4-alkylphenyl phosphite. Note that a minor amount of other alkylated hydroxyaryl compounds, e.g., ortho-substituted monoalkylated phenolics, may be included as an additional reactant in the above reaction scheme and would form additional derivative phosphites, but these additional reactants and products have been omitted from Reaction (VI) for clarity.

The compositions of the invention may be further processed into a variety of product forms, e.g., powder, granule, pellet, etc by a variety of known methods. The compositions may also be combined with one or more additional additives, fillers, primary antioxidants, etc., such as any of those described in detail below, in the production of these product forms or other multi-component additive packages.

Stabilizing Phosphite Compositions

As discussed above, a stabilizing amount or effective amount of the phosphite composition of the invention may be used as a secondary antioxidant for various types of polymers. As used herein, by "stabilizing amount" and an "effective amount" it is meant when the polymer composition containing the phosphite compositions of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to air heat, light, and/or other elements. In one example, improved stability is obtained in the form of one or both of lower initial color as measured by yellowing index and melt flow rate of the molten polymer or additional resistance to weathering, as measured, for example, by initial yellowness index (YI), or by resistance to yellowing and change in color, when compared to a composition without the stabilizer additive.

The additives and stabilizers described herein are preferably present in an amount effective to improve composition stability. When one of the aforementioned phosphite compositions is used, the composition is generally present in an amount from about 0.001 to about 5 wt. %, e.g., from about 0.0025 to about 2 wt. % or from about 0.005 to about 1 wt. %, based on the total weight of the polymer including the weight of the phosphite composition and any other stabilizers or additives. The phosphite compositions of this invention stabilize resins especially during high temperature processing with relatively little change in melt index and/or color, even after multiple extrusions.

The invention further relates to a stabilized thermoplastics, comprising a base polymer (e.g., polymer resin) and any of the aforementioned phosphite compositions of the invention. The polymer may be a polyolefin, and the solid phosphite composition may be used with a co-stabilizer, for example, hindered phenolics, aromatic amines, hydroxylamines, lactones, and thioethers. Thus, the thermoplastic that is stabilized by the phosphite compositions of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxidized soybean oils, the hydroxylamines, the tertiary amine oxides, lactones, thermal reaction products of tertiary amine oxides, and the thiosynergists.

In one embodiment, the amount of each component in the stabilizing composition, based on the total weight percent of the polymer or polymeric resin, is shown in Table 1.

TABLE 1

| Component | Range | Preferred Range |
|---|---|---|
| Solid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating or clarifying agents | 0-3.0 wt % | 0.001-2.0 wt % |
| Aminoxy propanoate | 0-3.0 wt % | 0.001-2.0 wt % |

Primary antioxidants include, for example:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6,-tricyclohexyphenol, and 2,6-di-tert-butyl-4-methoxymethylphenol. Commercially available alkylated monophenols include Lowinox™ 624 and Naugard™ 431. Other phenols are commercially available as BHEB.

(ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4octadecyloxyphenol. Commercially available alkylated hydroquinones include Lowinox AH25.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methyphenol). Commercially available hydroxylated thiodiphenyl ethers include Lowinox TBM6, and Lowinox TBP6.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2- hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl) terephthalate. Commercially available alkylidene-bisphenols include Lowinox 22M46, Lowinox WSP, Lowinox 44B25, Naugard 536, Naugawhite™, and Lowinox 22IB46.

(v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790.

(vi) Acylaminophenols, for example, 4-hydroxylauric acid amilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis[methylene{3,5-di-tert-butyl-4-hydroxycinnamate}] methane. Commercially available esters include Anox 20, Anox 1315, Lowinox GP45, Naugalube 38, Naugalube 531, Anox PP18, Naugard PS48 and Naugard XL-1.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24.

(x) Other phenolic antioxidants include the following phenols. Polymeric phenols such as the reaction product of 4-methylphenol with dicyclopentadiene and isobutylene, commercially available as Lowinox CPL. Alkylidene-poly-phenols, such as 1,3 tris(3-methyl-4-hydroxyl-5-t-butyl-phenyl)-butane (Lowinox CA22). Thio phenols such as 2,6-di-tert-butyl-4-(4,6-bis(octylthio)-1,3,5-triazin-2-ylamino)phenol (Irganox™ 565), 4,6-bis(octylthiomethyl)-o-cresol (Irganox 1520); 4,6-bis(dodecylthiomethyl)-o-cresol (Irganox 1726). Ester phenols include bis[3,3-bis(4-hydroxy-3-tert-butyl phenyl)butanoic acid]glycol ester (Hostanox™ O3). Still other phenols include 2-[1-(2-hydroxy-3,5-di-tert-pentylphenyl)ethyl]-4,6-di-tert-pentylphenyl acrylate (Sumilizer GS).

(xi) Hydroxyl amines, such as bis(octadecyl)hydroxylamine (Irgastab™ FS 042).

In one embodiment, the stabilizing composition comprises one primary antioxidant selected from the group consisting of tetrakismethylene(3,5-di-t-butyl-4-hydroxylhydrocinnamate)methane (Anox 20), 1,3,5-tris(3,5-di-t-butyl-4-hydroxybenzyl)isocyanurate (Anox IC-14), 1,3,5-tris(4-tert.-butyl-3-hydroxy-2,6-dimethylbenzyl)-1,3,5-triazine-2,4,6-(1H,3H,5H)-trione (Lowinox 1790), octyl-3-(3,5-di-t-butyl-4-hydroxyphenyl)propionate (Anox PP18), bis(octadecyl) hydroxylamine (Irgastab FS-042), 1,3,5-trimethyl-2,4,6-tris (3,5-di-tert-4-hydroxybenzyl) benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the phosphite composition defined herein.

The phosphite compositions and/or the resulting stabilized polymeric compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'methyl-, 3'-sec-butyl-5'tert-butyl-,4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy- 4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(ll).

(vi) Sterically hindered amines may be used as UV absorbers and light stabilizers. Sterically hindered amines, for example bis(2,2,6,6-tetramethylpiperidyl)-sebacate, bis-(1, 2,2,6,6-pentamethylpiperidyl)-sebacate, n-butyl-3,5-di-tert-butyl-4-hydroxybenzyl malonic acid bis(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94.

(vii) Oxalic acid diamides, for examples, 4,4'-dioctyloxyoxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o- and p-methoxy- as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis(2,4-dicumylphenyl)pentaerythritol diphosphite, and tetrakis(2,4-di-tert-butylphenyl)4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite); Doverphos™ 4, Doverphos 4-HR, Doverphos 4-HR Plus, Doverphos HiPure 4, and Doverphos S-9228; and Hostanox PEPQ.

(iii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer resin and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N, N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis(N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, dyes, optical brighteners, flameproofing agents, anti-static agents, blowing agents and thiosynergists such as dilaurythiodipropionate or distearylthiodipropionate.

Optionally the polymer or polymeric resins may include from 5-50 wt %, e.g., 10-40 wt % or 15-30 wt % fillers and reinforcing agents, for example, calcium carbonate, silicates, glass fibers, asbestos, talc, kaolin, mica, barium sulfate, metal oxides and hydroxides, carbon black and graphite.

The invention further pertains to a stabilized polymer, wherein one component comprises a solid phosphite composition of the present invention and the other a polymer, such as a polyolefin, polyvinyl chloride, etc., or polymeric resins.

The polymer stabilized by such solid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with solid phosphite compositions of the present invention are produced using a variety of polymerization processes including solution, high-pressure, slurry and gas phase using various catalysts including Ziegler-Natta, single-site, metallocene or Phillips-type catalysts. Non-limiting polymers useful with the solid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I21/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with solid phosphite compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the solid phosphite compositions are used in various rubber based products such as tires, barriers and the like.

In one embodiment, the solid phosphite compositions are suitable and/or approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

The polymer may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite mixtures of the present invention. These include polymers such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2-(2,2,4(4-hydroxyphenyl)-propane)terephthalate and polyhydroxybenzoates as well as block copolyetheresters derived from polyethers having hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the solid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

Other Applications

In another embodiment, it may be desirable to react the phosphite composition to form a new derivative product, that may have additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner. In view of the many changes and modifications that can be made without departing from the principles underlying the invention, reference should be made to the appended claims for an understanding of the scope of the protection to be afforded the invention. The present invention will now be further described by way of the following non-limiting examples.

EXAMPLES

Example 1

Solid Phosphite Prepared from a Mixture of 4-tert-Butylphenol and 2,4-Di-tert-butylphenol 2,4-Di-tert-butylphenol (93.3 g, 0.45 mols), 4-tert-butylphenol (17.0 g, 0.11 mols) and N,N-di-methyl-dodecylamine (2.47 mls, 9 mmols) were charged to an oil jacketed flask and heated to 90° C. under nitrogen. $PCl_3$ (25.0 grams, 0.18 mols) was added, below the surface of the phenolics, at a uniform rate over three hours. During the addition, the temperature was ramped to 150° C. The reaction mass was held at 150° C. until HCl evolution ceased, and then heated to 200° C. over one hour while the pressure was reduced from 1000 to 50 mbar. The reaction was held at 200° C./50 mbar until the total Cl content was less than 50 ppm. The phenolic excess and amine catalyst are then removed by distillation under 1 mbar pressure and an internal temperature of 225° C. The molten material was cast and allowed to cool to room temperature. During cooling, the mixed phosphite composition solidified. Yield=97.6 grams.

HPLC analysis revealed that the composition of the solid phosphite to be;

| | |
|---|---|
| Tris(2,4-di-tert-butylphenyl) phosphite | 46.7% |
| Bis(2,4-di-tert-butylphenyl)-4-tert-butylphenyl phosphite | 39.8% |
| 2,4-di-tert-butylphenyl-bis(-4-tert-butylphenyl) phosphite | 9.8% |
| Tris(4-tert-butylphenyl) phosphite | 0.7% |

The phosphite composition of example 1 softened and became mobile at 46 to 48° C. DSC analysis revealed the final endothermic event occurred at 152° C. (heat of fusion of ca −19.5 J/g). In comparison tris(2,4-di-tert-butylphenol)phosphite showed no signs of softening until its melt range of 180-185° C. was reached. DSC analysis revealed an endothermic event at 188° C. (heat of fusion determined to be ca 65 J/g).

DSC analysis was performed under nitrogen at a heating rate of 10° C./min, and the temperatures quoted were taken at the peak maxima.

Example 2

Solid Phosphite Prepared from a Mixture of 4-tert-Butylphenol and 2,4-Di-tert-butylphenol 2,4-Di-tert-butylphenol (108.25 g, 0.52 mols), 4-tert-butylphenol (8.75 g, 0.06 mols) and N,N-di-methyl-dodecylamine (2.47 mls, 9 mmols) were charged to an oil jacketed flask and heated to 90° C. under nitrogen. $PCl_3$ (25.0 grams, 0.18 mols) was added, below the surface of the phenolics, at a uniform rate over three hours. During the addition, the temperature was ramped to 150° C. The reaction mass was held at 150° C. until HCl evolution ceased, and then heated to 200° C. over one hour while the pressure was reduced from 1000 to 50 mbar. The reaction was held at 200° C./50 mbar until the total Cl content was less than 50 ppm. The phenolic excess and amine catalyst were then removed by vacuum distillation. The molten material was cast and allowed to cool to room temperature. During cooling, the mixed phosphite composition solidified. Yield=80.3 grams.

HPLC analysis revealed that the composition of the solid phosphite to be;

| | |
|---|---|
| Tris(2,4-di-tert-butylphenyl) phosphite | 65.9% |
| Bis(2,4-di-tert-butylphenyl)-4-tert-butylphenyl phosphite | 25.6% |
| 2,4-di-tert-butylphenyl-bis(-4-tert-butylphenyl) phosphite | 6.4% |
| Tris(4-tert-butylphenyl) phosphite | 0.4% |

The phosphite composition of example 2 became mobile at 163° C. DSC analysis revealed the final endothermic event occurred at 165° C. (heat of fusion of ca −40 J/g).

DSC analysis was performed under nitrogen at a heating rate of 10° C./min, and the temperature quoted was taken at the peak maxima.

Example 3

Solid Phosphite Prepared from a Mixture of 4-tert-Amylphenol and 2,4-Di-tert-amylphenol 2,4-Di-tert-amylphenol (117.1 g, 0.50 mols), 4-tert-amylphenol (9.1 g, 0.06 mols) and N,N-di-methyl-dodecylamine (2.47 mls, 9 mmols) were charged to an oil jacketed flask and heated to 90° C. under nitrogen. PCl₃ (25.0 grams, 0.18 mols) was added, below the surface of the phenolics, at a uniform rate over three hours. During the addition, the temperature was ramped to 150° C. The reaction mass was held at 150° C. until HCl evolution ceased, and then heated to 200° C. over one hour while the pressure was reduced from 1000 to 50 mbar. The reaction was held at 200° C./50 mbar until the total Cl content was less than 50 ppm. The phenolic excess and amine catalyst were then removed by vacuum distillation. The molten material was cast and allowed to cool to room temperature. During cooling, the mixed phosphite composition solidified. Yield=84.9 grams.

HPLC analysis revealed that the composition of the solid phosphite to be;

| | |
|---|---|
| Tris(2,4-di-tert-amylphenyl) phosphite | 71.3% |
| Bis(2,4-di-tert-amylphenyl)-4-tert-amylphenyl phosphite | 22.9% |
| 2,4-di-tert-amylphenyl-bis(-4-tert-amylphenyl) phosphite | 3.5% |
| Tris(4-tert-amylphenyl) phosphite | <0.25% |

The mixed phosphite composition was found to melt (by DSC) at 81.4° C. DSC analysis was performed under nitrogen at a heating rate of 10° C./min, and the temperature quoted was taken at the peak maxima.

Example 4

Preparation of a Butylated Phenol Alkylate with a High Di-tert-butylphenol Content Amberlyst 15 (15.0 g) was washed with molten phenol (4×50 g). After the final wash, the Amberlyst 15/phenol slurry was charged to a pre-heated (90° C.) jacketed vessel under nitrogen. Additional molten phenol was charged to the vessel such that the total amount of phenol used was 150 g (1.59 moles), and the mixture heated to 90° C. with stirring. 2-Methylpropene (189.7 g, 3.38 mols) was added over 3 hours at a uniform rate, below the surface of the phenol using a sintered glass frit. Once the addition was complete, the reaction was held at 90° C. to allow for transalkylation. After 3 hours the Amberlyst 15 was allowed to settle. The butylated phenol was decanted away from resin and then filtered to remove fines. Yield of crude butylated phenol=272.0 g.

The crude butylated phenol were charged to a vacuum fractional distillation equipment. The un-alkylated phenol and any residual water were removed by distillation; this was considered completed when the water content was less than 50 ppm and the phenol content was less than 0.5%. Distillation was continued to yield a main fraction (204.3 g) of butylated phenol alkylate that comprised <0.1 wt % phenol; 0.31 wt % 2-tert-butylphenol; 19.8 wt % 4-tert-butylphenol; 78.2 wt % 2,4-di-tert-butylphenol (1.7 wt % butylated phenol byproducts).

Example 5

A Solid Phosphite Prepared from a Butylated Phenol Alkylate with a High Di-Tert-Butylphenol Content Butylated phenol alkylate prepared in example 4 (112.6 g, 0.58 mols) was charged to a pre-heated (100° C.) jacketed vessel under nitrogen. The butylated phenol was heated to 100° C. with stirring and N,N-dimethyl-dodecyl amine (2.47 ml, 9 mmols) added. Phosphorus trichloride (25 g, 0.18 mols) was added at a uniform rate below the surface of the butylated phenol over a period of 3 hours. During the addition the temperature was ramped from 100° C. to 150° C. Once all the phosphorus trichloride had been added the reaction mass was held 150° C. for 1 hour. The reaction mass was then heated from 150° C. to 200° C. over 1 hour. Once the reaction was at 200° C. it was degassed by applying vacuum (60-80 mbar of pressure) until the total chlorine content was less than 50 ppm. The excess butylated phenol was removed by distillation under a pressure of 1.5 mbar up to an internal temperature of 250° C. (maximum vapour temperature 125° C.), until the free phenolics content <1000 ppm. The molten distillation residue was cast affording a white solid phosphite. The yield of phosphite=88.5 g.

HPLC analysis revealed that the composition of the solid phosphite to be;

| | |
|---|---|
| Tris(2,4-di-tert-butylphenyl) phosphite | 35.6% |
| Bis(2,4-di-tert-butylphenyl)-4-tert-butylphenyl phosphite | 42.8% |
| 2,4-di-tert-butylphenyl-bis(-4-tert-butylphenyl) phosphite | 13.3% |
| Tris(4-tert-butphenyl) phosphite | 1% |

What is claimed is:

1. A composition comprising a phosphite composition, which phosphite composition consists of:
   (a) from 25 to 80 weight percent of a tris(dialkylaryl) phosphite;
   (b) from 15 to 50 weight percent of a bis(dialkylaryl) monoalkylaryl phosphite;
   (c) from 3 to 25 weight percent of a bis(monoalkylaryl) dialkylaryl phosphite;

(d) from 0.1 to 6 weight percent of a tris(monoalkylaryl) phosphite;

(e) from 0 to 5 weight percent other phosphites wherein dialkylaryl in (a), (b), (c) and (d) is dibutylphenyl or diamylphenyl and monoalkaryl in (a), (b), (c) and (d) is butylphenyl or amylphenyl, weight percent is based on the total weight of all phosphites in the phosphite composition, and wherein the phosphite composition is a solid at ambient conditions melting in a temperature range of from greater than 30° C. to less than 170° C.

2. The composition of claim 1, wherein the phosphite composition contains from 0.1 to 5% weight percent other phosphites selected from the group consisting of phosphites containing trialkylaryl moieties and phosphites containing unsubstituted aryl moieties.

3. The composition of claim 2, wherein the phosphite composition contains 0.1 to 4 weight percent of trialkyl aryl moieties.

4. The composition of claim 1, wherein the phosphite composition comprises components (a) and (b) in combination in an amount greater than 74 weight percent, based on the total weight of all phosphites in the phosphite composition.

5. The composition of claim 1, wherein at least 55 weight percent of all dialkylaryl and monoalkaryl moieties in the phosphite composition are phenyl substituted with alkyl groups in both the ortho-position and the para-position.

6. The composition of claim 1, wherein dialkylaryl in (a), (b), (c) and (d) is di-t-butylphenyl and monoalkaryl in (a), (b), (c) and (d) is t-butylphenyl.

7. The composition of claim 1, wherein dialkylaryl in (a), (b), (c) and (d) is di-t-amylphenyl and monoalkaryl in (a), (b), (c) and (d) is t-amylphenyl.

8. A phosphite composition prepared by reacting a phosphorus halide with an alkylated phenol composition comprising a monoalkylphenol in an amount from 2 to 45 weight percent, and a dialkylphenol in an amount from 55 to 98 weight percent, based on the total weight of all alkylated phenols in the alkylated phenol composition, wherein alkyl moieties on the monoalkylphenol and the dialkylphenol are selected from the group consisting of isomers of butyl and amyl and the phosphite composition which is prepared comprises:

(a) a tris(dialkylaryl)phosphite in an amount from 20 to 93 weight percent;

and at least one of:

(b) a bis(dialkylaryl)monoalkylaryl phosphite;

(c) a bis(monoalkylaryl)dialkylaryl phosphite; and (d) a tris(monoalkylaryl)phosphite, wherein the composition comprises components (b), (c) and (d) in combination in an amount from 7 to 80 weight percent, based on the total weight of all phosphites in the composition, which composition comprises 0 to 5 weight percent other phosphites, and wherein a composition consisting of (a), at least one of (b), (c) and (d) and between 0 to 5 weight percent other phosphites is a solid at ambient conditions melting in a temperature range of from greater than 30° C. to less than 170° C.

9. The phosphite composition of claim 8 wherein the alkylated phenol composition is prepared by contacting one or more butene or pentene olefins with a phenol in the presence of a catalyst and under conditions effective to form the alkylate composition, wherein the molar ratio of the one or more olefins to the phenol is from 1.25:1 to 3:1.

10. The phosphite composition of claim 8 wherein the alkylated phenol composition comprises a dialkylphenol in an amount ranging from 60 to 95 weight percent and a monoalkylphenol in an amount ranging from 5 to 40 weight percent based on total weight of all alkylated phenols in the alkylated phenol composition.

11. The phosphite composition of claim 9, wherein at least 50 weight percent of alkyl moieties in the alkylated phenol composition are t-butyl.

12. The phosphite composition of claim 9, wherein at least 50 weight percent of alkyl moieties in the alkylated phenol composition are tert-amyl.

13. A composition according to claim 1 further comprising a polymer.

14. The composition of claim 1, wherein at least 55 weight percent of aryl moieties comprised by the phosphites are substituted with alkyl groups in both the ortho-position and the para-position, at least 10 weight percent are monosubstituted in the para-position, 0.1 to 3 weight percent are trisubstituted and 0.1 to 3 weight percent are mono-substituted in the ortho position.

* * * * *